United States Patent
Metselaar

(10) Patent No.: US 10,471,010 B2
(45) Date of Patent: Nov. 12, 2019

(54) LIPOSOMAL CORTICOSTEROIDS FOR TREATMENT OF INFLAMMATORY DISORDERS IN HUMANS

(71) Applicant: ENCELADUS PHARMACEUTICALS B.V., Naarden (NL)

(72) Inventor: Josbert Maarten Metselaar, Naarden (NL)

(73) Assignee: ENCELADUS PHARMACEUTICALS B.V., Naarden (NL)

( * ) Notice: Subject to any disclaimer, the term of this patent is extended or adjusted under 35 U.S.C. 154(b) by 673 days.

(21) Appl. No.: 14/355,845

(22) PCT Filed: Nov. 2, 2012

(86) PCT No.: PCT/NL2012/050766
§ 371 (c)(1),
(2) Date: May 2, 2014

(87) PCT Pub. No.: WO2013/066179
PCT Pub. Date: May 10, 2013

(65) Prior Publication Data
US 2015/0050329 A1    Feb. 19, 2015

Related U.S. Application Data

(63) Continuation-in-part of application No. PCT/NL2011/050755, filed on Nov. 4, 2011.

(51) Int. Cl.
*A61K 9/127* (2006.01)
*A61K 31/573* (2006.01)
(Continued)

(52) U.S. Cl.
CPC .......... *A61K 9/1271* (2013.01); *A61K 9/0019* (2013.01); *A61K 31/573* (2013.01); *A61K 45/06* (2013.01)

(58) Field of Classification Search
CPC ...................................... A61K 9/127
See application file for complete search history.

(56) References Cited

U.S. PATENT DOCUMENTS 5,783,211 A * 7/1998 Manzo .................. A61K 8/14
                                              424/450
7,955,618 B2 * 6/2011 Metselaar ............ A61K 9/1271
                                              424/450
(Continued)

FOREIGN PATENT DOCUMENTS

EP     2127639 A1    12/2009
JP   H04-500676 A     6/1992
(Continued)

OTHER PUBLICATIONS

Office Action issued in co-pending Japanese Patent Application No. 2014-539900, dated Aug. 2, 2016, with English translation.
(Continued)

*Primary Examiner* — Gollamudi S Kishore
(74) *Attorney, Agent, or Firm* — Sunit Talapatra; Foley & Lardner LLP

(57) ABSTRACT

The invention relates to a pharmaceutical composition comprising liposomes composed of non-charged vesicle-forming lipids, optionally including not more than 10 mole percent of negatively charged vesicle-forming lipids and/or not more than 10 mole percent of PEGylated lipids, the liposomes having a selected mean particle diameter in the size range of 40-200 nm and comprising a first corticosteroid in water soluble form, for the site-specific treatment of inflammatory disorders in humans, providing in human patients a fast, strong, and durable anti-inflammatory effect
(Continued)

for at least 2 weeks at a dose of at most 5 mg/kg body weight of prednisolone or an equipotent dose corticosteroid other than prednisolone at a treatment frequency of at most once per two weeks. Furthermore the present invention relates to the application of the above-mentioned pharmaceutical composition given as intervention therapy in inflammatory disorders such as rheumatic disease or a related inflammatory connective tissue disorder, inflammatory diseases of the kidney or inflammatory bowel disorders, in combination with chronic therapy with a second free corticosteroid formulation or in combination with chronic treatment with a disease-modifying agent such as methotrexate.

13 Claims, 7 Drawing Sheets

(51) Int. Cl.
*A61K 9/00* (2006.01)
*A61K 45/06* (2006.01)

(56) References Cited

U.S. PATENT DOCUMENTS

| | | | |
|---|---|---|---|
| 2002/0102293 A1* | 8/2002 | Sachse | A61K 9/1277 424/450 |
| 2004/0014782 A1* | 1/2004 | Krause | A61K 31/16 514/313 |
| 2006/0147511 A1 | 7/2006 | Panzner et al. | |
| 2008/0020991 A1* | 1/2008 | Mathis | C12N 15/117 514/44 A |
| 2008/0113907 A1* | 5/2008 | Rosewicz | A61K 38/1709 536/23.1 |
| 2009/0148442 A1* | 6/2009 | Ponce, Jr. | A61K 39/395 424/133.1 |
| 2009/0274754 A1* | 11/2009 | Cipolla | A61K 9/0043 424/450 |
| 2010/0009952 A1 | 1/2010 | Lichter et al. | |

FOREIGN PATENT DOCUMENTS

| | | |
|---|---|---|
| JP | 2004-517835 A | 6/2004 |
| JP | 2005-534663 A | 11/2005 |
| JP | 2006-509750 A | 3/2006 |
| WO | 02/45688 A2 | 6/2002 |
| WO | 03/105805 A1 | 12/2003 |
| WO | 2006/060759 A2 | 6/2006 |

OTHER PUBLICATIONS

International Search Report for PCT/NL2012/050766, dated Jan. 17, 2013.
Elron-Gross I et al: "Liposomal dexamethasone-diclofenac combinations for local osteoarthritis treatment", International Journal of Pharmaceutics, Elsevier BV, NL, vol. 376, No. 1-2, Jul. 6, 2009, pp. 84-91, XP026185230, ISSN: 0378-5173, DOI: 10.1016/J.IJPHARM. 2009.04.025.
For the Fin-Raco Trial Group Mottonen T el al: "Comparison of combination therapy with single-drug therapy in early rheumatoid arthritis: a rondomised trial", The Lancet, Lancet Limited. London, GB, vol. 353, No. 9169, May 8, 1999, pp. 1568-1573, XP004825956, ISSN: 0140-6736, DOI: 10.1016/S0140-6736(98) 08513-4.
Office Action issued in co-pending Japanese Patent Application No. 2014-539900, dated Mar. 7, 2017, with English translation.
Harashima et al., "Species Difference in the Disposition of Liposomes Among Mice, Rats, and Rabbits: Allometric Relationship and Species Dependent Hepatic Uptake Mechanism", Pharm. Res., 1996, vol. 13, No. 7, pp. 1049-1054.

* cited by examiner

LIPOSOMAL CORTICOSTEROIDS FOR TREATMENT OF INFLAMMATORY DISORDERS IN HUMANS

The invention relates to the field of medicine. More specifically the invention relates to corticosteroid treatment of inflammatory disorders.

Inflammatory diseases like inflammatory connective tissue disorder, such as rheumatoid arthritis (RA), inflammatory diseases of the kidney and inflammatory bowel disorders (IBD) are chronic, progressive, and debilitating diseases often leading to disability. Prednisolone and other corticosteroids can be effective in inflammatory diseases, but their systemic application is limited because of a high incidence of adverse effects (AE) including osteoporosis, hypothalamic-pituitary-adrenal axis (HPA) suppression, muscle wasting, insulin resistance, easy skin bruising, increased risk of serious bacterial infections, and cardiovascular events. In most cases the severity of these AE depends on dose, duration of exposure and potency of the prescribed agent. Besides a poor safety profile, also poor localization in inflamed areas in the body limits the usefulness of corticosteroids in the patient, as this requires frequent administration of corticosteroids to attain adequate therapeutic benefit.

In recent years, several lines of investigation have been pursued to improve the therapeutic index of corticosteroids. These lines encompass for instance the development of selective glucocorticoids (GC) receptor agonists (SEGRAs), the combination of corticosteroids with drugs that potentiate their effects in activated inflammatory cells, the development of controlled-release formulations, and the design of advanced formulations that achieve targeted delivery of corticosteroids to the actual sites of inflammation. Targeted delivery of corticosteroids can be realized by encapsulation in long circulating liposomes (LCL) that circulate after i.v. injection and at the same time extravasate at the sites of inflammation lesions by virtue of increased vascular permeability, building local depots of corticosteroids selectively at the target sites. This approach is for instance described in WO 02/45688 and WO 03/105805 and proved to be effective in preclinical studies with experimental animal models of arthritis, and other inflammatory diseases.

Typically in these experiments PEG-liposomal prednisolone phosphate (PLP) at a dose of 10 mg/kg of PLP results in resolution of the inflammation up to one week after treatment, after which the inflammation slowly comes back. 20 mg/kg PEG-liposomal prednisolone phosphate can lead to a resolution of the inflammation still observable 2 weeks after treatment. Single treatment with an equal dose of free prednisolone is not effective while repeated daily treatment with free prednisolone only results in a short-lasting moderate effect as shown by the results of the study under Example 1 (FIGS. 1A and 1B).

However, intravenous administration of liposomal corticosteroid at dose levels of 10 and 20 mg/kg of a corticosteroid in humans is impractical. If a dose of 20 mg prednisolone per kg body weight is administered to an individual with a body weight of 75 kg a total of 1.5 g of prednisolone is administered. The typical prednisolone content of formulations with liposomal prednisolone is 1.5 mg of prednisolone per mL. As a result, a dose of 20 mg prednisolone per kg body weight would require one liter (1.5 g prednisolone/ 1.5 mg/mL) of formulation per treatment. Such amount of formulation then needs to be infused over more than 12 hours to prevent infusion or hypersensitivity reactions, i.e. pseudoallergic reactions that can be caused by intravenous administration of particles such as liposomes to humans.

Furthermore, these high prednisolone doses lead to the administration of enormous quantities of liposomal components, such as phospholipid and cholesterol, to the patient. Lower doses of liposomal corticosteroid would therefore be preferred for the treatment of inflammatory disorders in humans, because in that case less of the liposomal corticosteroid formulation needs to be administered and administration times as long as 12 hours are not necessary. However, in animal studies, doses lower than 10 mg/kg liposomal prednisolone have a much less durable effect as is for instance demonstrated in Example 1 (FIGS. 2A and 2B). 1 mg/kg of prednisolone has a limited effect during 4 days only. 2 mg/kg of prednisolone shows the same effect duration although it is slightly more effective. Even at 5 mg/kg the therapeutic activity lasts no longer than 1 week.

Similar observations have been described in prior publications. For instance, WO 02/45688 describes that a dose of 10 mg/kg liposomal prednisolone phosphate was effective in rats with adjuvant-induced arthritis. Although it is mentioned that 1 mg/kg liposomal prednisolone phosphate was also effective, the duration of the therapeutic effect is, however, not indicated. The analogous scientific publication, Metselaar J M. et al. 2003, demonstrates that a dose of 1 mg/kg liposomal prednisolone phosphate has a therapeutic activity in rats with adjuvant-induced arthritis that lasts only 4 days (see FIG. 3A of Metselaar J M. et al.). A sustained treatment with a dose of 1 mg/kg in rats would thus require administration of the liposomal corticosteroid at least once every 4 days.

EP 2127639 describes the use of liposomal corticosteroid for treatment of cardiovascular disease. As an example, treatment of rabbits with aortic atherosclerotic plaques is described. The rabbits were treated with liposomal prednisolone phosphate at a dose of 15 mg/kg body weight, which resulted in a therapeutic effect lasting up to two weeks. Lower doses of liposomal corticosteroid were not tested or described.

WO 2006/060759 relates to the use of liposomal triamcinolone for treatment of the respiratory tract. It is described that administration via a nebulizer once every one to two weeks is allowed, without any indication as to the dose of the liposomal triamcinolone. The experimental section of WO 2006/060759 describes a mouse model of asthma. Mice were treated once a week with liposomal triamcinolone.

Thus, the prior art teaches that administration of a dose of at least 10 mg/kg body weight may result in a therapeutic effect in animal models of inflammatory disorders that lasts at least two weeks. Administration of a lower doses of liposomal corticosteroid in these animals may only have a satisfying therapeutic efficacy if treatment is given at a higher frequency, such as once every week or once every 4 days. Therefore, based on experiments performed in rats, mice and rabbits described in prior publications and in present Example 1, a person skilled in the art would expect that to achieve an effective therapeutic response, treatment at dose levels below 10 mg/kg of corticosteroid will need to be repeated at least within a week, possibly even every four days. Before the present invention, it was expected that with doses below 10 mg/kg of corticosteroid a lasting therapeutic response is not possible. At most short effects were expected, which require multiple doses of liposomal corticosteroid to be administered. In a clinical setting this means that at these low dose levels—because liposomal corticosteroids will be applied in an outpatient setting—the patient would need to go to the hospital every 4 to 7 days to receive a new intravenous infusion, which is not practical. In order for liposomal corticosteroid treatment to be feasible, a patient needs to achieve a lasting therapeutic response that allows him/her to go home after the treatment without the need to repeat the treatment, or at least without the need to come back to the hospital within the next 2 weeks or an even longer time period. Furthermore, the infusion time of the treatment preferably does not take longer than approximately 4 hours and therefore treatment need to be limited to maximally 200 mL of liposomal corticosteroid formulation. Finally, the treatment preferably allows the patient to continue with his/her maintenance therapy comprising for instance the relatively cheap and widely available small-molecular disease modifying agents (e.g. methotrexate, hydroxychloroquine, leflunomide, cyclophosphamide, 5-fluorouracil, a 5-ASA agent, 6-mercaptopurine, or azathioprine). Such disease modifying agents are not effective in and not used for suppressing a temporary exacerbation of inflammation but are rather used to modify the long-term course of the disease. Clinical practice has revealed that without an effective treatment of the short-term exacerbations of inflammation a patient will be likely to cease his/her maintenance therapy with the relatively cheap (generic) disease modifying agents and instead desire to commence therapy with the relatively expensive biological products (e.g. infliximab, enbrel, adalimumab, anakinra and related products). In contrast to disease modifying agents, such biological products can be effective in an acute setting but need to be used, like the disease modifying agents, as maintenance therapy. However, the costs of maintenance therapy with such biological products is many times larger than the cost of therapy with disease modifying agents and the tendency of patients to switch to biologicals can eventually lead to an enormous increase of the burden of healthcare costs.

It is an aim of the present invention to overcome the limitations mentioned above by providing liposomal corticosteroid formulations that can be used to achieve a long lasting and clinically meaningful therapeutic response in patients suffering from an exacerbation or an active phase of inflammatory disorder, such as inflammatory connective tissue disorders (notably rheumatoid arthritis), inflammatory diseases of the kidney or inflammatory bowel disorders. Accordingly, the invention provides in one aspect a method for the treatment of an inflammatory disorder in a human comprising administering to a human in need thereof a pharmaceutical composition comprising liposomes composed of non-charged vesicle-forming lipids, optionally including not more than 10 mole percent of negatively charged vesicle-forming lipids and/or not more than 10 mole percent of PEGylated lipids, the liposomes having a selected mean particle diameter in the size range of 40-200 nm and comprising a first corticosteroid in water soluble form in a dose of at most 5 mg/kg body weight of prednisolone or an equipotent dose of a corticosteroid other than prednisolone, wherein said treatment has a treatment frequency of at most once per two weeks. Also provided is a use of liposomes composed of non-charged vesicle-forming lipids, optionally including not more than 10 mole percent of negatively charged vesicle-forming lipids and/or not more than 10 mole percent of PEGylated lipids, the liposomes having a selected mean particle diameter in the size range of 40-200 nm and comprising a first corticosteroid in water soluble form for the preparation of a medicament for the treatment of an inflammatory disorder in a human at a dose of at most 5 mg/kg body weight of prednisolone or an equipotent dose of a corticosteroid other than prednisolone, wherein said treatment has a treatment frequency of at most once per two weeks.

Liposomes composed of non-charged vesicle-forming lipids, optionally including not more than 10 mole percent of negatively charged vesicle-forming lipids and/or not more than 10 mole percent of PEGylated lipids, the liposomes having a selected mean particle diameter in the size range of 40-200 nm and comprising a first corticosteroid in water soluble form, are herein also referred to as "liposomes for use in a method according to the invention" and "liposomes as defined herein".

A pharmaceutical composition comprising such liposomes is herein referred to as "a pharmaceutical composition for use in a method according to the invention" and "a pharmaceutical composition comprising liposomes as described herein".

The invention provides the insight that administration of liposomal corticosteroid at a dose of at most 5 mg/kg body weight of prednisolone or an equipotent dose of a corticosteroid other than prednisolone in humans suffering from an inflammatory disorder leads to a surprisingly long lasting therapeutic effect of up to 2 weeks or longer. As shown in Example 2, in rheumatoid arthritis (RA) patients a fast, strong, and durable anti-inflammatory activity is shown with a relatively low dose of 150 mg (roughly 2 mg/kg), which activity is comparable to the relatively new intravenous anti-TNF alpha biologicals that are currently on the market for these diseases (a drop of the EULAR DAS-28 score of 1.5 points). The long-lasting effect observed at this lower (and therefore clinically more practical) dose level is new as compared to the known preclinical study results at these dose levels in rats (see the comparison in FIG. 6 of the results from the preclinical study in rats under Example 1 with the results of the clinical study according to the present invention in humans reported under Example 2). In clinical practice this means that when a patient experiences an exacerbation or an active phase of an inflammatory disease, i.e. a disease flare, a single treatment may suffice to keep the disease flare under control. Alternatively, if repeated treatment is needed, a treatment frequency of once per two weeks or lower, as long as the exacerbation or active disease phase lasts, will suffice to keep the disease flare under control.

A pharmaceutical composition comprising liposomes for use in a method according to the invention is advantageously combined with a second pharmaceutical composition comprising a free corticosteroid. It was found by the present inventor that treatment with intravenous liposomal corticosteroids is complementary to treatment with intramuscular formulations of corticosteroid. As is demonstrated in Example 2, the therapeutic activity of the liposomal corticosteroid in humans suffering from RA is not only stronger as compared to an equipotent dose of free corticosteroid (methylprednisolone in Example 2) administered intramuscularly, but also faster. As is shown in FIGS. 3-5, the liposomal corticosteroid provides a fast and strong therapeutic response especially during the first weeks. It has its maximum therapeutic activity, i.e. maximum reduction of EULAR disease activity scores, within the first two weeks following administration, after which the scores gradually increase again. On the other hand, an intramuscular formulation of free corticosteroid leads to a moderate therapeutic response reached after some weeks. The therapeutic activity gradually increases following administration and reaches its maximum therapeutic activity at weeks three to seven following administration. Thus, intramuscularly administered free corticosteroid functions as a depot formulation. Combination of liposomal corticosteroid and free corticosteroid is therefore particularly advantageous because both a strong direct therapeutic activity as well as a strong therapeutic activity several weeks after administration are achieved. Thus, if such a combination is used, liposomal corticosteroid serves as a direct treatment of the inflammatory disorder and the free corticosteroid serves as a depot formulation, i.e. as a more slowly establishing treatment. Giving these two treatments at the same time therefore yields an efficacy profile over an even longer period of time (4-6 weeks or longer) so that repeated treatment with the liposomal formulation can be avoided for at least 4 weeks.

In one embodiment, the invention therefore provides a method for the treatment of an inflammatory disorder in a human comprising administering to a human in need thereof a pharmaceutical composition comprising liposomes as described herein, and a pharmaceutical composition comprising a second, free corticosteroid. A dose of at most 5 mg/kg body weight of prednisolone or an equipotent dose of a corticosteroid other than prednisolone, and a treatment frequency of liposomal corticosteroid of at most once per two weeks are preferred.

Also provided is a kit of parts comprising a pharmaceutical composition comprising liposomes as herein described, and a pharmaceutical composition comprising a second, free corticosteroid. Said kit of part further preferably comprises instructions for a dosing regime for the first, liposomal, corticosteroid of at most 5 mg/kg body weight of prednisolone or an equipotent dose of a corticosteroid other than prednisolone at a treatment frequency of at most once per two weeks, and, optionally, for a dosing regime for the second, free corticosteroid of between 0.5 and 5 mg/kg body weight of prednisolone or an equipotent dose of a corticosteroid other than prednisolone. It is preferred that the kit of parts comprises an amount of liposomal corticosteroid corresponding to the dosage regimen of at most 5 mg/kg body weight of prednisolone or an equipotent dose of a corticosteroid other than prednisolone with a treatment frequency of at most once per two weeks. Therefore, said kit of parts preferably comprises one or more dosage units, each dosage unit suitable for administration of the first, liposomal, corticosteroid at a dose of at most 5 mg/kg body weight of prednisolone or an equipotent dose of a corticosteroid other than prednisolone. Further, said kit of parts preferably comprises one or more dosage units, each dosage unit suitable for administration of the second, free corticosteroid at a dose of between 0.5 and 5 mg/kg body weight of prednisolone or an equipotent dose of a corticosteroid other than prednisolone.

Further provided is a combination of a pharmaceutical composition comprising liposomes as described herein, and a pharmaceutical composition comprising a second, free corticosteroid for use in a method for the treatment of an inflammatory disorder in a human, preferably at a dose of at most 5 mg/kg body weight of liposomal prednisolone or an equipotent dose of a liposomal corticosteroid other than prednisolone, wherein said treatment has a treatment frequency of at most once per two weeks.

"Free corticosteroid" as used herein refers to a corticosteroid that is not incorporated in a microvesicle such as a liposome. Optionally said free corticosteroid is coupled to a pharmaceutically acceptable carrier and/or present in a pharmaceutically acceptable diluent, optionally in the presence of one or more pharmaceutically acceptable additives. A second, free corticosteroid is preferably in fat soluble form and can be identical to the first, liposomal, corticosteroid, or different. Preferably a second free corticosteroid is a corticosteroid used in clinical practice for the treatment of inflammatory disorders in a human, being typically prednisolone, methylprednisolone, triamcinolone, dexamethasone, betamethasone, cortisone or their respective derivatives, such as prednisolone acetate, methylprednisolone acetate, triamcinolone acetate, betamethasone phosphate.

A pharmaceutical composition comprising said second free corticosteroid is preferable administered orally, intra-articularly, intravenously, subcutaneously, or most preferably, intramuscularly to a human in need thereof in a method according to the invention. A pharmaceutical composition comprising liposomes as described herein is preferably administered intravenously, more preferably by intravenous infusion.

If a combination treatment is used involving administration of liposomes as described herein and a second, free corticosteroid, said treatment preferably involves administration of a pharmaceutical composition comprising said liposomes at a dose of at most 5 mg/kg body weight of prednisolone or an equipotent dose of a corticosteroid other than prednisolone, at a treatment frequency of at most once per two weeks. Said second, free corticosteroid is preferably administered at a dose of between 0.5 and 5 mg/kg, preferably between 1 and 5 mg/kg, with a treatment frequency of at most once every two weeks. Most preferably, said first, liposomal corticosteroid and said second, free corticosteroid are administered concomitantly. With "concomitantly" it is meant that the first and the second corticosteroid are administered at the same time, or almost at the same time. The second, free corticosteroid is preferably administered within one hour before administration of the first liposomal corticosteroid is started, during administration of the first liposomal corticosteroid, or within one hour after administration of the first liposomal corticosteroid has finished, more preferably within 30 minutes before or after administration of the first liposomal corticosteroid, even more preferably within 15 minutes before or after administration of the first liposomal corticosteroid or during administration of the first liposomal corticosteroid.

A pharmaceutical composition comprising liposomes for use in a method according to the invention is also advantageously combined with a pharmaceutical composition comprising a disease modifying agent. According to the present invention, pharmaceutical compositions comprising liposomes for use in a method according to the invention, are particularly suitable for counteracting an active episode of an inflammatory disorder. Such pharmaceutical liposomal compositions provide an effective intervention therapy when a patient, who has an otherwise rather stable disease course as a result of sustained treatment with disease modifying agents, infrequently and unexpectedly experiences an active episode or an exacerbation of inflammation. A dose of at most 5 mg/kg body weight of prednisolone or an equipotent dose of a corticosteroid other than prednisolone, and a treatment frequency of liposomal corticosteroid of at most once per two weeks are preferred.

In one embodiment, the invention therefore provides a method for the treatment of an inflammatory disorder in a human comprising administering to a human in need thereof a pharmaceutical composition comprising liposomes as described herein, and a pharmaceutical composition comprising a disease modifying agent. Said treatment comprises maintenance therapy with said pharmaceutical composition comprising a disease modifying agent and temporary therapy of an exacerbation of inflammation with a pharmaceutical composition comprising liposomal corticosteroids.

Also provided is a combination of a pharmaceutical composition comprising liposomes as described herein, and a pharmaceutical composition comprising a disease modifying agent for use in a method for the treatment of an inflammatory disorder in a human.

As detailed in Example 2, it was found that patients suffering from rheumatoid arthritis who receive maintenance therapy with methotrexate are more sensitive to therapy with liposomal corticosteroid than patients who do not take methotrexate or who take another disease modifying agent. In spite of the fact that the treatment of corticosteroids in combination with methotrexate is not unheard of in the literature, the clinical trial reported in Example 2 shows that patients who received intramuscularly administered free corticosteroid in combination with methotrexate did not show a better response than patients with intramuscularly administered free corticosteroid without methotrexate (FIG. 7). In contrast, according to the invention, a combination of liposomal corticosteroid and methotrexate does provide better results as compared to liposomal corticosteroids alone. Thus, a combination of liposomes as described herein with methotrexate maintenance therapy is highly effective in reducing disease activity, whereas treatment of such patients with a combination of free corticosteroid and methotrexate is not. In clinical practice this means that patients, who are otherwise successfully treated by maintenance therapy with relatively cheap oral disease modifying agents like methotrexate and go through an active phase or an exacerbation of the disease can now be very effectively treated with a single infusion, or only a few repeated infusions, with liposomal corticosteroid. This allows patients with a low frequency of disease flaring to quickly regain the low activity phase of the disease and to continue with their relatively cheap disease modifying agent therapy without the desire or need to switch to treatment with the more expensive biologicals that more recently entered the field of inflammatory diseases. Besides the convenience for the patient, this is also important from a health economics perspective as treatment which entails the use of liposomal corticosteroid helps to keep the costs associated with treatment of inflammatory diseases within limits.

Therefore, in a preferred embodiment, a human suffering from an inflammatory disorder receives maintenance therapy with a pharmaceutical composition comprising a disease modifying agent and receives temporary treatment with a pharmaceutical composition comprising liposomes following a flare of said inflammatory disorder.

The term "disease modifying agent" is known in the art and refers to a small molecular drug used as maintenance therapy in inflammatory diseases, i.e. it is taken by a patient for a prolonged period of time as to modulate the progression of the disease, usually longer than one month but more typically longer than three months. For instance, disease modifying agents used in the treatment of rheumatoid arthritis are disease-modifying antirheumatic drugs (DMARDs). Such small molecular drug used as maintenance therapy in inflammatory diseases preferably has a molecular weight of at most 800 dalton. Preferably a disease modifying agent for use in a method according to the invention is chosen from the group of relatively cheap disease modifying agents given in clinical practice for the sustained treatment of inflammatory diseases, such as methotrexate, hydroxychloroquine, leflunomide, cyclophosphamide, 5-fluorouracil, a 5-ASA agent, 6-mercaptopurine, mycophenolate mofetil, and azathioprine. In a particularly preferred embodiment, the disease modifying agent is methotrexate. If the disease treated in accordance with the invention is a rheumatic disease or a related inflammatory connective tissue disorder, said disease modifying agent is preferably selected from the group consisting of methotrexate, hydroxychloroquine, leflunomide, cyclophosphamide, 5-fluorouracil, a 5-ASA agent, 6-mercaptopurine, and azathioprine, most preferably said disease modifying agent is methotrexate. If the disease treated in accordance with the invention is an inflammatory disease of the kidney, said disease modifying agent is preferably selected from the group consisting of hydroxychloroquine, mycophenolate mofetil, azathioprine and cyclophosphamide. If the disease treated in accordance with the invention is an inflammatory bowel disorder, said disease modifying agent is preferably selected from the group consisting of a 5-ASA agent, azathioprine, 6-mercaptopurine and methotrexate.

"Maintenance therapy" as used herein refers to therapy which is received by a patient for a prolonged period of time as to modulate the progression of the disease, usually longer than one month but more typically longer than three months. Typically, maintenance therapy involves administration of a daily dose of a medicament, such as a disease modifying agent.

"Temporary treatment" as used herein refers to treatment which is received by a patient via a single dose or a limited number of doses, i.e. less than 10, preferably less than 5, such as two or three doses. "Temporary treatment" is used herein to discriminate the treatment from "maintenance therapy", which, as indicated above, entails treatment for a prolonged period of time.

"A flare" as used herein refers to a period during which an inflammatory disorder enters into an active phase or exacerbates, and thus to an increase in severity of the manifestations of the disorder.

Preferably, a pharmaceutical composition comprising a disease modifying agent is administered orally, in the form of tablets, capsules or elixirs for oral administration. A pharmaceutical composition comprising liposomes as described herein is preferably administered intravenously, more preferably by intravenous infusion. If a combination treatment is used involving administration of liposomes as described herein and a disease modifying agent, said treatment preferably involves administration of a pharmaceutical composition comprising said liposomes at a dose of at most 5 mg/kg body weight of corticosteroid, at a treatment frequency of at most once per two weeks.

"Treatment frequency" as used herein refers to the frequency of administration of (a pharmaceutical composition comprising) liposomes for use in a method according to the invention. For instance, a treatment frequency of once per two weeks means that a pharmaceutical composition is administered to a patient once every two weeks, i.e. administration of two different doses is separated by approximately two weeks. In clinical practice, this may be two weeks plus or minus one or two days. A treatment frequency of at most once per two weeks indicates that a pharmaceutical composition is administered to a patient once every two weeks or often less, such as once every three weeks, or once every four weeks. Thus, the time between two doses is at least two weeks, or a second dose is not administered at all. A sole and single administration of a pharmaceutical composition as described herein is also encompassed within the term "treatment frequency of at most once per two weeks".

According to the present invention, the dose of a pharmaceutical composition comprising liposomes for use in a method according to the invention is at most 5 mg/kg body weight of prednisolone or an equipotent dose of a corticosteroid other than prednisolone. "Equipotent dose" as used herein is defined as the dose of a corticosteroid required to produce the same pharmacological effect as compared to the pharmacological effect of a given dose of prednisolone. For instance, if a dose of prednisolone is 2.5 mg/kg, an equipotent dose of another corticosteroid is the dose that has the same pharmacological effect as 2.5 mg/kg of prednisolone. The term "pharmacological effect" refers to the effect of a corticosteroid on a human body, preferably to a therapeutic effect. Methylprednisolone and triamcinolone have a potency ratio of 1.25 as compared to prednisolone. "A potency ratio" as used herein refers to the ratio of the pharmacological effect of a corticosteroid to that of prednisolone, whereby the potency of prednisolone is set to 1. Thus, a corticosteroid having a potency ratio of 1.25 indicates that a dose of 5/1.25=4 mg/kg of said corticosteroid has an effect comparable to the effect of a dose of 5 mg/kg of prednisolone. Said dose of 4 mg/kg is thus an equipotent dose of 5 mg/kg of prednisolone. As said before, methylprednisolone and triamcinolone have a potency ratio of 1.25 as compared to prednisolone. Therefore, in one embodiment, a liposome for use in a method according to the invention comprises methylprednisolone or triamcinolone and said dose is at most 4 mg/kg body weight of methylprednisolone or triamcinolone. Dexamethasone and betamethasone have a potency ratio of 6.5 as compared to prednisolone. Therefore, in another embodiment, a liposome for use in a method according to the invention comprises dexamethasone or betamethasone and said dose is at most 0.8 mg/kg body weight of dexamethasone or betamethasone, because said dose is a dose equipotent to 5 mg/kg body weight of prednisolone. As another example, fludrocortisone acetate has a potency ratio of 3.5 as compared to prednisolone. Therefore, in another embodiment, a liposome for use in a method according to the invention comprises fludrocortisone acetate and said dose is at most 1.4 mg/kg body weight of fludrocortisone acetate, because said dose is a dose equipotent to 5 mg/kg body weight of prednisolone.

The dose may be typically 4 mg/kg of prednisolone or an equipotent dose of a corticosteroid other than prednisolone, or lower, such as a dose of at most 3.5 mg/kg of prednisolone or an equipotent dose of a corticosteroid other than prednisolone, or a dose of at most 3 mg/kg of prednisolone or an equipotent dose of a corticosteroid other than prednisolone. Doses of at most 2.5 mg/kg body weight of prednisolone or an equipotent dose corticosteroid other than prednisolone are preferred. Examples of preferred doses are 2.5 mg/kg, 2 mg/kg, 1.5 mg/kg and 1 mg/kg. In one embodiment, a liposome for use in a method according to the invention comprises methylprednisolone or triamcinolone and said dose is at most 2 mg/kg body weight of methylprednisolone or triamcinolone. In another embodiment, a liposome for use in a method according to the invention comprises dexamethasone or betamethasone and said dose is at most 0.4 mg/kg body weight of dexamethasone or betamethasone. In yet another embodiment, a liposome for use in a method according to the invention comprises fludrocortisone acetate and (a pharmaceutical composition comprising) said dose is at most 0.7 mg/kg body weight of fludrocortisone acetate. The above mentioned doses are all doses equipotent to 5 mg/kg body weight of prednisolone. Most preferably, said dose is at most 2.5 mg/kg body weight of prednisolone.

Treatment may be repeated after two weeks, however treatment intervals of three weeks, four weeks or longer are also possible. Alternatively, a single treatment with a pharmaceutical composition for use in a method according to the invention having a dose of at most 5 mg/kg of prednisolone or an equipotent dose corticosteroid other than prednisolone is used if such single treatment is sufficient to overcome the active episode or the exacerbation of the inflammatory disease in the human, preferably said dose is at most 4 mg/kg, more preferably at most 3 mg/kg, more preferably at most 2.5 mg/kg.

A pharmaceutical composition comprising liposomes, free corticosteroid or a disease modifying agent for use in a method according to the invention preferably further comprises a pharmaceutically acceptable carrier, diluent and/or excipient.

Liposomes for use in a method according to the invention have a mean particle diameter of 40-200 nm as determined by Dynamic Light Scattering using Malvern DLS measurement laser equipment. Preferably the liposomes have a diameter of between 75 and 150 nm. The liposomes preferably have a rather low polydispersity index, i.e. of below 0.2, which means that the particle size distribution is narrow.

Liposomes for use in a method according to the present invention typically comprise non-charged vesicle forming lipids from the group of phospholipids, that can be either artificially synthesized or that originates from a natural source, optionally being artificially modified. Preferably said non-charged vesicle forming lipids are partially or wholly synthetic. Phosphatidylcholines (PC), including those obtained from natural sources or those that are partially or wholly synthetic, or of variable lipid chain length and unsaturation are suitable for use in the present invention. As used herein, the term "partially synthetic or wholly synthetic vesicle-forming phospholipids" means at least one vesicle-forming phospholipid which has either been artificially made or which originates from a naturally occurring phospholipid, which has been artificially modified. Preferred phospholipids contain saturated alkyl chains yielding a bilayer with a relatively high transition temperature. Particularly preferred are DiPalmitoyl Phosphatidyl Choline (DPPC), Hydrogenated Soy Bean Phosphatidyl Choline (HSPC), DiStearoyl Phosphatidyl Choline (DSPC), and Hydrogenated Egg Phosphatidyl Choline (HEPC). Liposomes for use in a method according to the present invention comprise at most 10 mole % PEGylated lipids and/or at most 10 mole % of negatively charged lipids. Preferred PEGylated lipids are composed of a PEG polymer with a molecular mass between 200 and 20 000 dalton on the one end and a lipophilic anchoring molecule on the other end. Typically anchoring molecules are chosen from the group of phospholipids and sterols. Preferred PEGylated lipids are PEG 2000-DiStearoyl Phosphatidyl Ethanolamine (PEG-DSPE) and PEG 2000-cholesterol. Preferred negatively charged lipids are DiPalmitoyl Phosphatidyl Glycerol (DPPG) and DiStearoyl Phosphatidyl Glycerol (DSPG).

Liposomes for use in a method according to the present invention further preferably comprise a sterol or steroid alcohol of synthetic or natural origin which have a hydroxyl group in the 3-position of the A-ring. Of this group of sterol compounds cholesterol is preferred.

The fraction of polymer lipid conjugates and negatively charged lipids is 0-10 mol %, and preferably 1-10 mol %, more preferably 2.5-10 mol %, based upon the total molar ratio of the vesicle forming lipids in the formulation. The presence of negatively charged lipids and especially polymer-lipid-conjugates in the liposomal formulation stabilizes the formulation and has a favourable effect on the circulation time of the liposome. However, by carefully selecting specific lipid compositions at physical specifications, suitable long circulation times can be obtained without using a PEG-lipid-conjugate or negatively charged lipids. For example, 50-100 nm liposomes of DSPC and cholesterol and/or sphingolipids like sphingomyelin are suitable for use in a method according to the invention.

In a particularly preferred embodiment, the invention provides a liposome for use according to the invention or a method according to the invention, wherein said liposome comprises 0-50 mol % of cholesterol, 50-90 mol % of non-charged partially synthetic or wholly synthetic vesicle-forming lipids, 0-10 mol % of amphipatic vesicle-forming lipids coupled to polyethylene glycol, and 0-10 mol % of a negatively charged vesicle-forming lipid. Such liposome is for instance made in accordance with the methods described in WO 02/45688 or WO 03/105805. However, low doses and treatment frequencies in accordance with the present invention are not described therein. Liposomes for use in a method according to the invention preferably have a mean particle diameter size range of between about 75 and 150 nm. As stated before, said partially synthetic or wholly synthetic vesicle-forming lipid is preferably selected from the group consisting of DSPC, DPPC, HSPC and HEPC.

Specific examples of liposomes for use in a method according to the invention are:

liposomes composed of non-charged vesicle-forming lipids, including up to 10 mole percent of an amphipathic vesicle-forming lipid derivatised with polyethyleneglycol and optionally including not more than 10 mole percent of negatively charged vesicle-forming lipids, which liposomes have a selected mean particle diameter in the size range of 40-200 nm and containing a corticosteroid, characterised in that the corticosteroid is present in a water soluble form;

liposomes composed of cholesterol and non-charged vesicle-forming lipids selected from DSPC, HSPC, HEPC and DPPC, which liposomes have a selected mean particle diameter in the size range of 40-200 nm and contain a corticosteroid characterised in that the corticosteroid is present in a water soluble form;

liposomes composed of non-charged vesicle-forming lipids and not more than 5 mole percent of negatively charged dipalmitoyl phosphatidyl glycerol, which liposomes have a selected mean particle diameter in the size range of 40-200 nm and contain a corticosteroid characterised in that the corticosteroid is present in a water soluble form;

liposomes composed of cholesterol and non-charged vesicle-forming lipids selected from phospholipids that are partially or wholly synthetic, optionally including not more than 5 mole percent of negatively charged vesicle-forming lipids, which liposomes have a selected mean particle diameter in the size range of 40-200 nm and contain a corticosteroid characterised in that the corticosteroid is present in a water soluble form.

As said, liposomes used in accordance with the present invention may be prepared according to methods used in the preparation of conventional liposomes or PEG-liposomes, for instance such as disclosed in WO 02/45688 or WO 03/105805. Passive loading of the active ingredients into liposomes by dissolving the corticosteroids in the aqueous phase is sufficient in order to reach sufficient encapsulation, but other methods can also be used, so as to further increase the encapsulation efficiency. The lipid components used in forming the liposomes may be selected from a variety of vesicle-forming lipids, such as phospholipids, sphingolipids and sterols. Substitution (complete or partial) of these basic components by e.g. sphingomyelins and ergosterol appeared to be possible. For effective encapsulation of the water-soluble corticosteroids in liposomes, thereby avoiding leakage of the drug from the liposomes, especially phospholipid components having saturated, rigidifying acyl chains have appeared to be useful.

A liposomal composition for use in a method according to the present invention comprises a water-soluble corticosteroid. The term "water-soluble" is defined herein as having a solubility at a temperature of 25° C. of at least 10 g/l water or water buffered at neutral pH. Water soluble corticosteroids which can be advantageously used in accordance with the present invention are alkali metal and ammonium salts prepared from corticosteroids, having a free hydroxyl group, and organic acids, such as (C2-C12) aliphatic, saturated and unsaturated dicarbonic acids, and inorganic acids, such as phosphoric acid and sulphuric acid. As alkaline metal salts the potassium and sodium salts are preferred. Also other, positively or negatively charged, derivatives of corticosteroids can be used. Specific examples of water soluble corticosteroids are betamethasone sodium phosphate, desonide sodium phosphate, dexamethasone sodium phosphate, hydrocortisone sodium phosphate, hydrocortisone sodium succinate, methylprednisolone disodium phosphate, methylprednisolone sodium succinate, pre dnisolone sodium phosphate, pre dnisolone sodium succinate, pre dnisolamate hydrochloride, prednisone disodium phosphate, prednisone sodium succinate, triamcinolone acetonide disodium phosphate and triamcinolone acetonide disodium phosphate. Of these corticosteroids, prednisolone disodium phosphate, pre dnisolone sodium succinate, methylprednisolone disodium phosphate, methylprednisolone sodium succinate, dexamethasone disodium phosphate and betamethasone disodium phosphate are preferred. The above-mentioned corticosteroids normally are used in systemic treatment of anti-inflammatory diseases and disorders. In one embodiment therefore, the first corticosteroid comprises within a liposomes for use in a method according to the invention and/or the second, free corticosteroid is a corticosteroid for systemic administration. As used herein "a corticosteroid for systemic administration" means that said corticosteroid is in clinical practice used in systemic treatment of anti-inflammatory diseases.

Since it has been proved that by using a water-soluble form of a corticosteroid in long-circulating liposomes, having a mean particle diameter of 40-200 nm, effective targeting of the drug to inflammation sites occurs, the present invention can also advantageously be applied to corticosteroids, which for a variety of reasons normally are used for topical use. Such corticosteroids include for example alclomethasone dipropionate, amcinonide, beclomethasone monopropionate, betamethasone 17-valerate, ciclomethasone, clobetasol propionate, clobetasone butyrate, deprodone propionate, desonide, desoxymethasone, dexamethasone acetate, diflucortolone valerate, diflurasone diacetate, diflucortolone, difluprednate, flumetasone pivalate, flunisolide, fluocinolone acetonide acetate, fluocinonide, fluocortolone pivalate, fluormetholone acetate, fluprednidene acetate, halcinonide, halometasone, hydrocortisone acetate, medrysone, methylprednisolone acetate, mometasone furoate, parametasone acetate, prednicarbate, pre dnisolone acetate, prednylidene, rimexolone, tixocortol pivalate and triamcinolone hexacetonide. Topical corticosteroids of special interest are e.g. budesonide, flunisolide and fluticasone propionate, which undergo fast, efficient clearance as soon as these drugs become available in the general circulation. By preparing a water soluble form of these steroids and encapsulating this into long-circulating liposomes in accordance with the present invention it is now possible to systemically administer such corticosteroids in order to reach site-specific drug delivery, thereby avoiding adverse effects associated with systemic treatment and overcoming problems, which are inherent to the corticosteroid, such as a fast clearance. In this respect budesonide disodium phosphate has appeared to be a salt of great interest. In one embodiment therefore, the first corticosteroid comprised within a liposome for use in a method according to the invention and/or the second, free corticosteroid is a corticosteroid for topical application. As used herein "a corticosteroid for topical application" means that said corticosteroid is in clinical practice used in topical treatment of anti-inflammatory diseases, i.e. it is applied body surfaces such as the skin or mucous membranes such as those from the vagina, anus, throat and eyes.

Examples of inflammatory disorders that can be successfully treated with the liposomal compositions in accordance with the present invention are inflammatory connective tissue disorders, inflammatory diseases of the kidney and inflammatory bowel disorders (IBD). Specific examples of inflammatory connective tissue disorders are rheumatoid arthritis, systemic lupus erythomatosis (with for instance lupus nephritis as one of its notable manifestations), alkylosing spondylitis, osteoarthritis, and psoriatic arthritis. Preferably an inflammatory disorder treated with a method according to the present invention is a rheumatic disease, more preferably rheumatoid arthritis, or an inflammatory bowel disorder, or an inflammatory disease of the kidney. Of the inflammatory bowel disorders, colitis ulcerosa and Crohn's disease are preferred inflammatory disorders treated in accordance with the present invention. Preferred inflammatory diseases of the kidney treated in accordance with the present invention are glomerulonephritis, lupus nephritis, acute transplant rejection and arteriovenous fistula failure.

The invention is further explained in the following examples. These examples do not limit the scope of the invention, but merely serve to clarify the invention.

A. Effect on macroscopic paw inflammation scores of a single treatment with 10 mg/kg PLP-polyethylene glycol (PEG) liposomes (solid circles), 10 mg/kg free PLP (solid squares), and saline control treatment (open squares).

B. Effect on scores of 20 mg/kg PLP-polyethylene glycol (PEG) liposomes (solid circles), daily treatment with 20 mg/kg free PLP (solid squares) and saline control (open squares). Bars show the mean and SEM of 5 rats. Treatment took place on day 14.

Figure 2A:
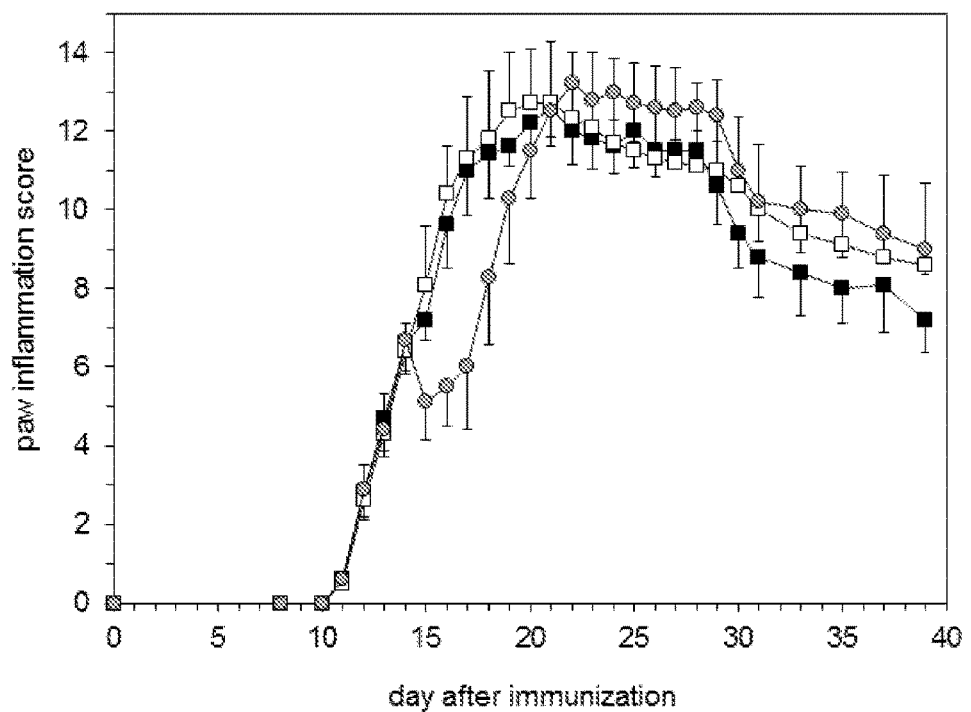

FIG. 2. Therapeutic activity of a single treatment with increasing dose levels of prednisolone phosphate (PLP)-polyethylene glycol (PEG) liposomes in rats with adjuvant-induced arthritis.

A. Effect on macroscopic paw inflammation scores of 1 mg/kg PLP-PEG liposomes (grey circles), 10 mg/kg free PLP (solid squares), and saline control treatment (open squares).

B. Effect on scores of 2 mg/kg PLP-PEG liposomes (grey circles), 5 mg/kg PLP-PEG liposomes (solid squares), and saline control (open squares).

Bars show the mean and SEM of 3-5 rats. Treatment took place on day 14 (A) and day 13 (B).

Figure 3:
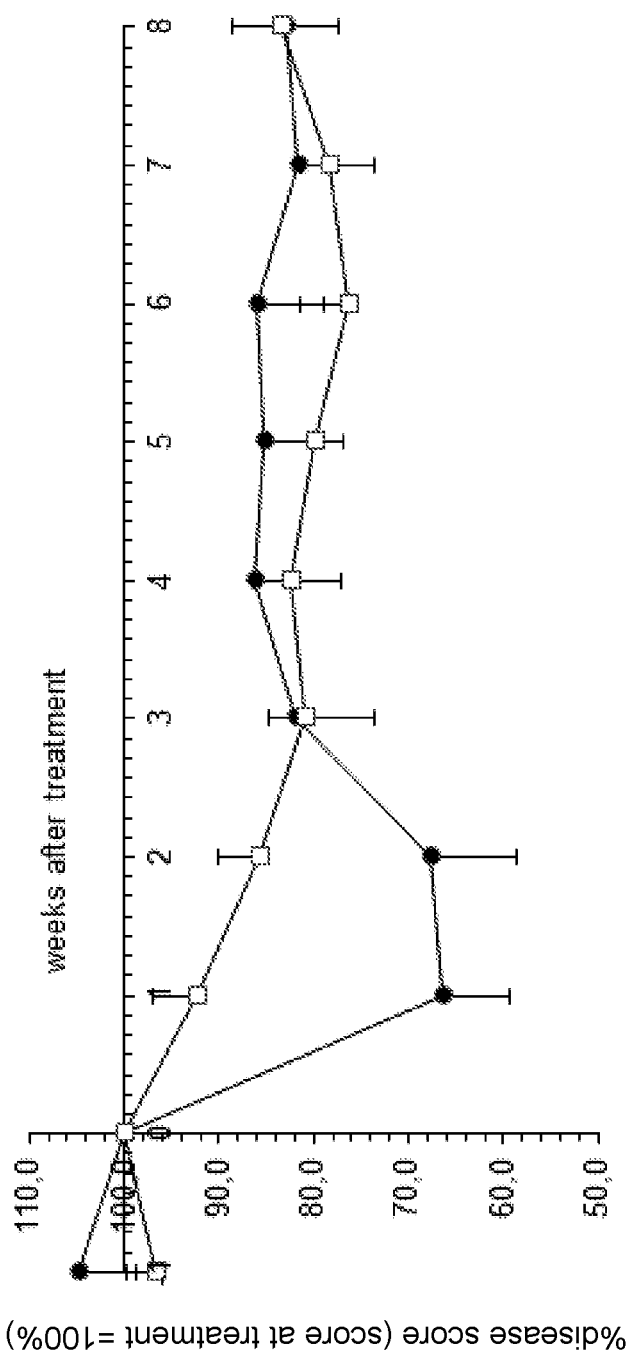

FIG. 3. Effect on EULAR Disease Activity Scores (DAS 28 scores) of 150 mg (2 mg/kg) PLP-PEG-liposomes (solid circles) and an equipotent dose of 120 mg (1.6 mg/kg) methylprednisolone (intramuscular depot formulation, open squares). Bars show the mean and SEM of 7 human subjects in both treatment groups. The values are expressed as % of the disease score at day of treatment (baseline), the baseline defined as 100%.

Figure 4:
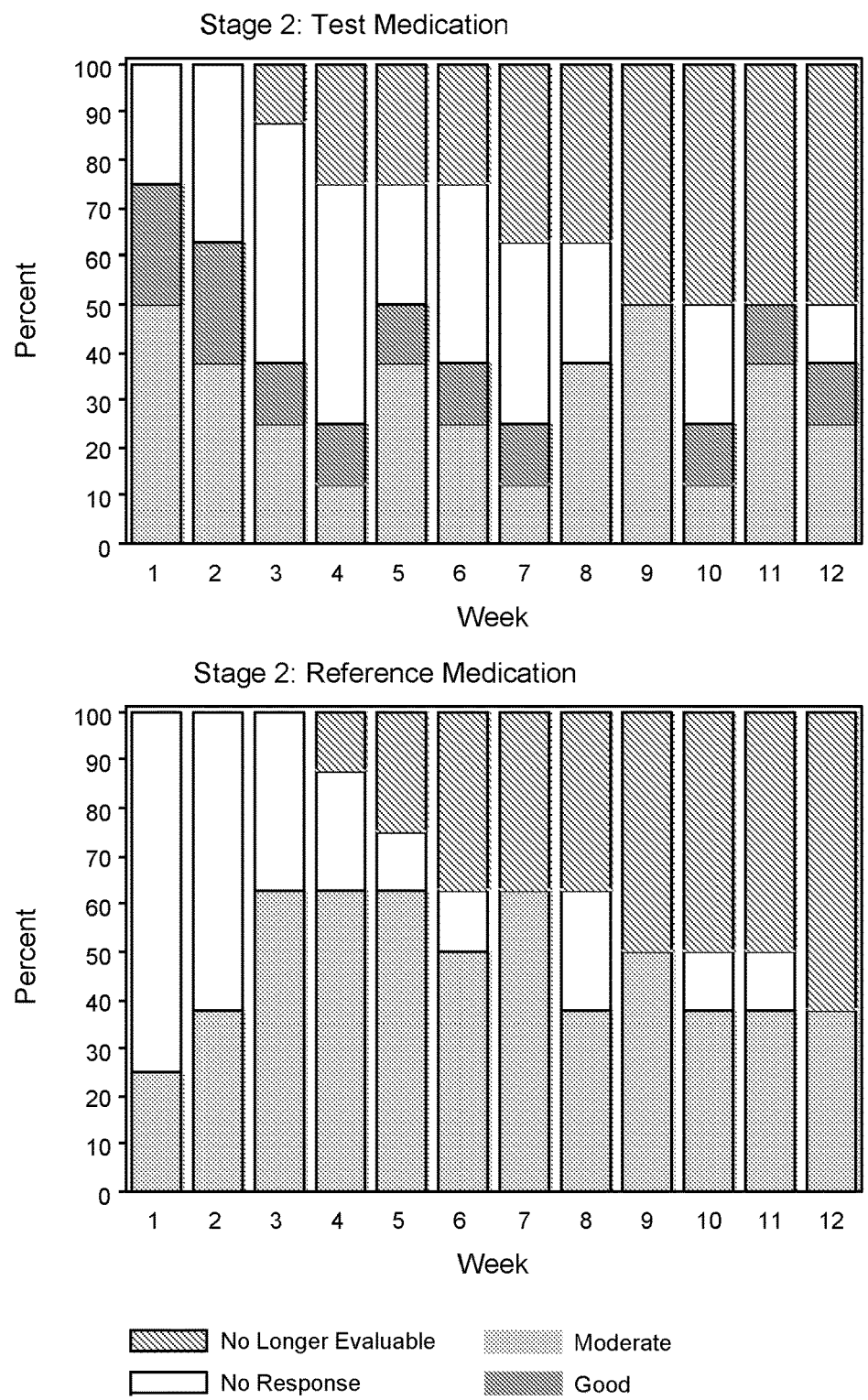

FIG. 4. Distribution of patients achieving a good, moderate or no EULAR response after 150 mg (2 mg/kg) PLP-PEG-liposomes (test medication) or an equipotent dose of 120 mg (1.6 mg/kg) methylprednisolone (reference medication). Bars show the mean of 7 human subjects in both treatment groups.

Figure 5:
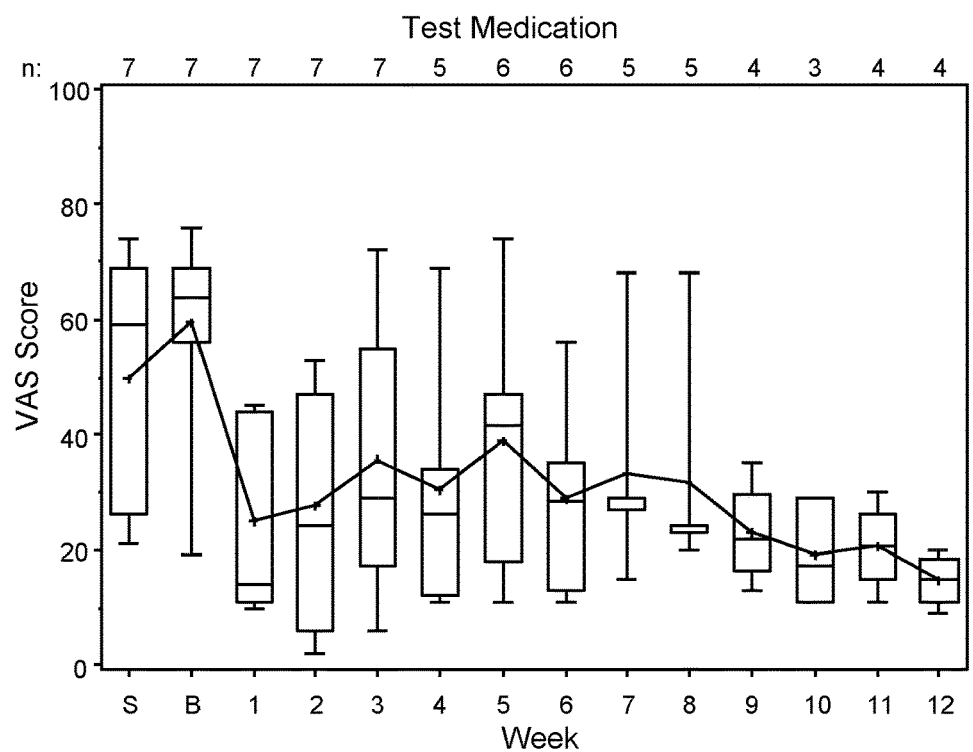
Figure 5:
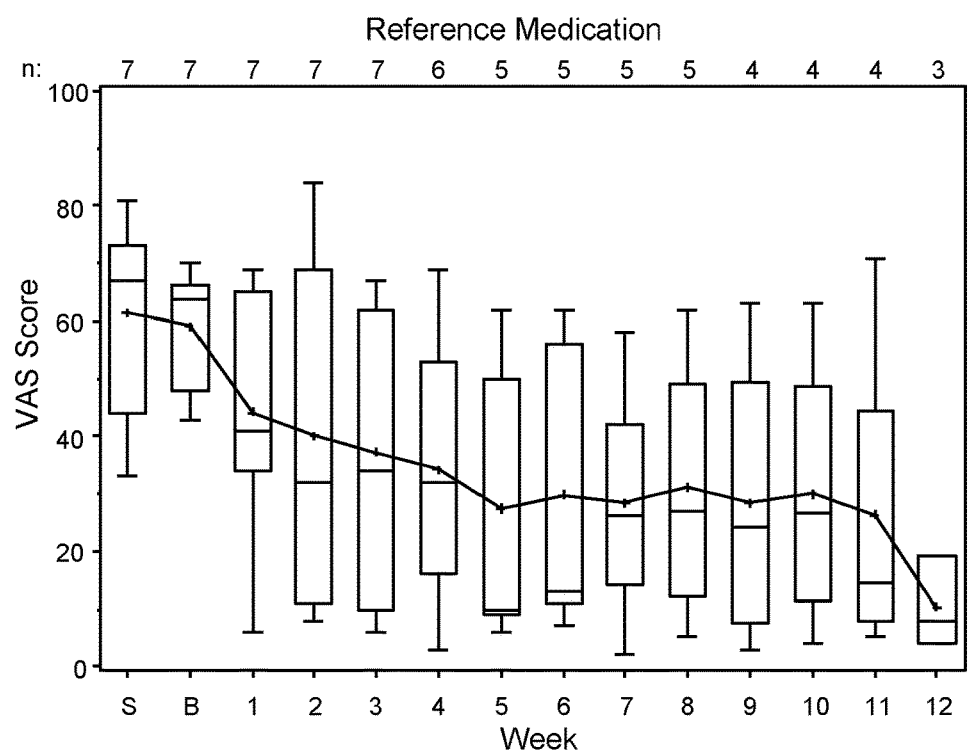

FIG. 5. Intensity of pain as determined by VAS score after 150 mg (2 mg/kg) PLP-PEG-liposomes (test medication) or an equipotent dose of 120 mg (1.6 mg/kg) methylprednisolone (reference medication).

Bars show the mean and SEM of 7 human subjects in both treatment groups. The values are expressed as % of the VAS score at day of treatment.

FIG. 6. Therapeutic activity of a single treatment with 2 mg/kg prednisolone phosphate (PLP) PEG-liposomes in rats versus humans.

A. Effect in rats on macroscopic disease scores as a % of baseline (100%).

B. Effect in humans on EULAR Disease Activity Scores (DAS 28 scores) as a % of baseline (100%).

Bars show the mean and SEM of 3-5 rats (A) and 7 humans (B).

FIG. 7. Effect on EULAR Disease Activity Scores (DAS 28 scores) of a single treatment of:

A. 150 mg (2 mg/kg) PLP-PEG-liposomes to patients who receive chronic methotrexate therapy (solid circles, n=4) compared to patients who do not take methotrexate (open squares, n=3).

B. An equipotent dose of 120 mg (1.6 mg/kg) methylprednisolone (intramuscular depot formulation) to patients who receive chronic methotrexate therapy (solid circles, n=4) compared to patients who do not take methotrexate (open squares, n=3). Bars show the mean and SEM. The values are expressed as % of the disease score at day of treatment (baseline), the baseline defined as 100%.

EXAMPLES

Example 1

Rat Experimental Arthritis Study

Formulation

Prednisolone phosphate-containing PEG-liposomes were composed of 750 mg of dipalmitoyl phosphatidylcholine (DPPC), 250.8 mg of cholesterol and 267.6 mg of PEG-distearoylphosphatidylethanol-amine (PEG-DSPE). These components were weighed and mixed in a 100 ml round-bottom flask. The lipids were dissolved in about 30 ml of ethanol and thereafter evaporated to dryness in a Rotavapor during 1 hour under vacuum at 40° C. 1200 mg of prednisolon disodium phosphate was weighed and dissolved in 12 ml of sterilized water. The solution was added to the dry lipid film and shaken during one hour in the presence of glass beads in order to enable complete hydration of the lipid film. The liposomal suspension was transferred to an extruder (Avestin, maximum volume 15 ml) and extruded under pressure, using nitrogen gas, using polycarbonate filters with pore sizes below 100 nm. Subsequently the liposomal suspension was dialyzed against sterile saline. The mean particle size of the liposomes was determined by dynamic light scattering and was found to be 93.1±1.2 nm, the polydispersity index being 0.095±0.024. The encapsulation efficiency of the prednisolone phosphate was determined by means of a HPLC method and was found to be between 3 and 4%. The suspension of liposomes was stored in a nitrogen atmosphere at 4° C. and found to be stable for more than a year.

Rats, Experimental Arthritis and Study Protocol

Lewis rats were immunized subcutaneously at the tail base with heat-inactivated *Mycobacterium tuberculosis* in incomplete Freund's adjuvant. Paw inflammation started between 9 and 12 days after immunization, reached maximum severity approximately after 20 days, and then gradually resolved. Assessment of the disease was performed by visually scoring paw inflammation severity, maximum score 4 per paw, and measuring disease-induced body weight loss. The therapeutic efficacy of liposomal prednisolone phosphate on these variables was compared with equal doses unencapsulated drug. Rats were treated when the average score >6 (at day 14 or 15 after disease induction).

Results

Figure 1A:
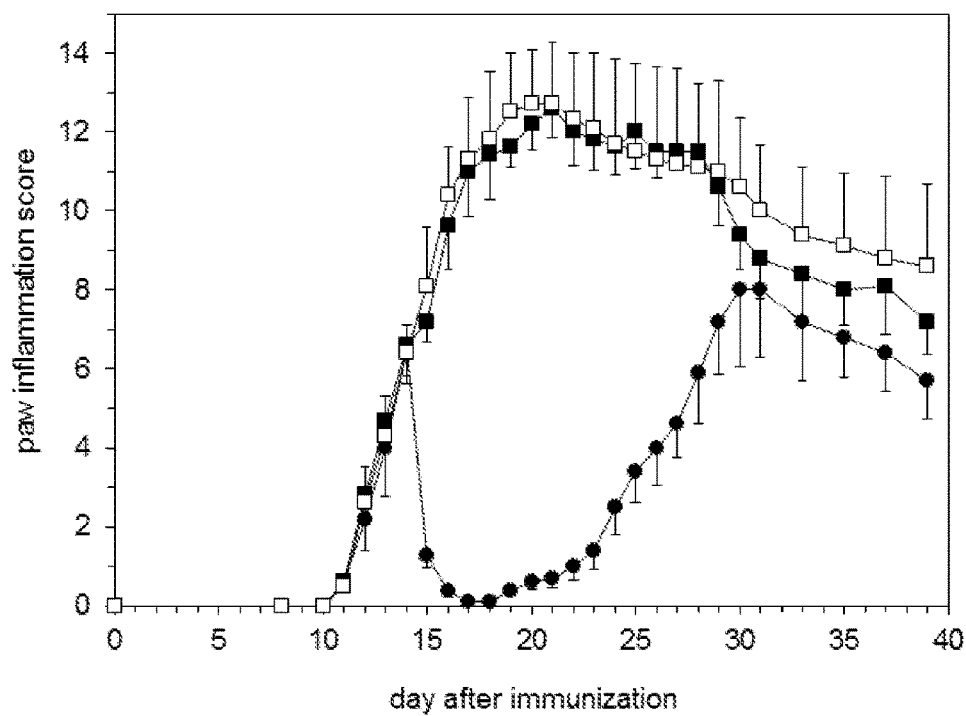
FIG. 1. Therapeutic activity of treatment with liposomal and free prednisolone phosphate (PLP) in rats with adjuvant-induced arthritis.
Figure 1B:
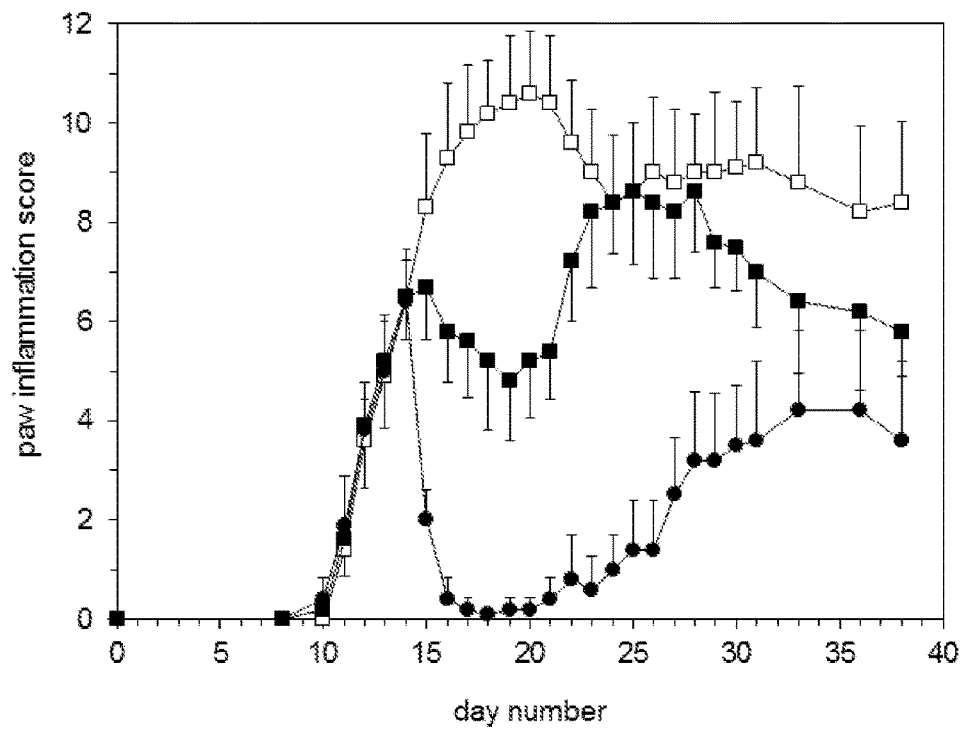

A complete remission of the inflammation in 4 out of 5 rats was observed within 3 days after treatment with a single dose of liposomal prednisolone phosphate at 10 mg/kg of prednisolone phosphate (FIG. 1A). Unencapsulated prednisolone phosphate did not significantly alter the course of the disease as a single injection. Therefore it was decided to inject an even higher dose of 20 mg/kg unencapsulated prednisolone daily for 7 days. This treatment regimens reduced inflammation scores from an average of 6.5 (day 14) to average values around 5.0 from day 15 until day 21 (control treatment with daily saline reached a maximum of 10.6 on day 20, FIG. 1B). However, a single injections of the same dose of 20 mg/kg liposomal prednisolone phosphate at day 14 resulted in disappearance of adjuvant arthritis (AA) symptoms until day 20.

Figure 2B:
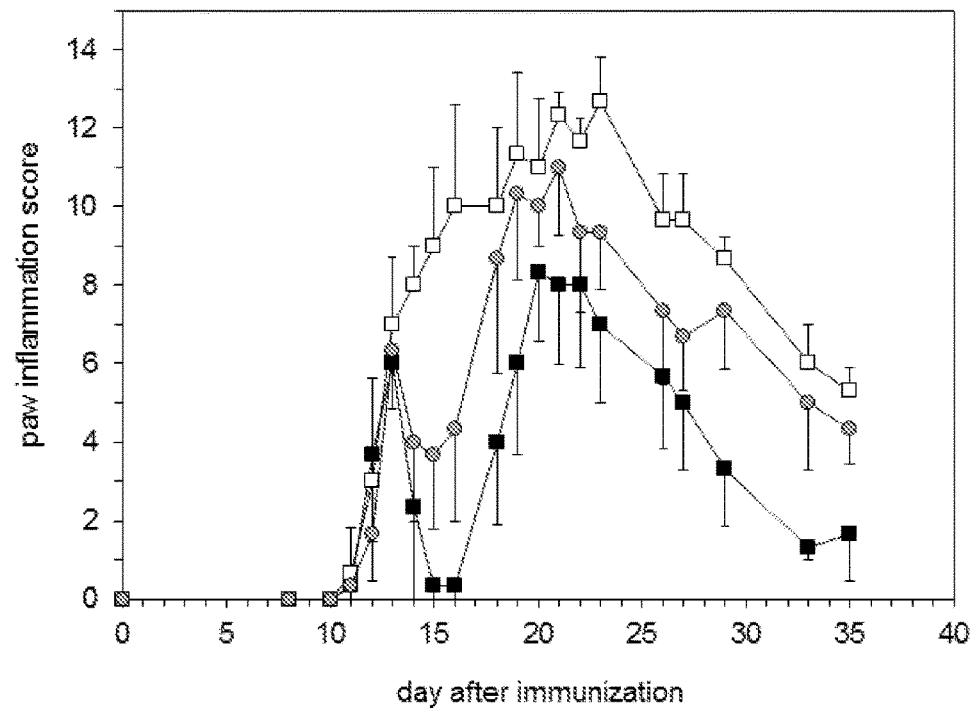

Also dose levels lower than 10 mg/kg liposomal prednisolone were tested in the rat adjuvant arthritis model. The efficacy at these dose levels proved to be short lasting. 1 mg/kg liposomal prednisolone has a limited effect during 4 days only (FIG. 2A), while 2 mg/kg shows the same effect duration albeit slightly more effective (FIG. 2B). Even at 5 mg/kg the therapeutic activity lasts no longer than 1 week (FIG. 2B).

Example 2

Human RA Study

Formulation

Prednisolone containing polyethylene glycol (PEG) liposomes are composed of a lipid bilayer enclosing an aqueous compartment in which the water-soluble disodium phosphate derivative of prednisolone is entrapped. Each mL of formulation contains 1.5 mg/mL prednisolone sodium phosphate, 30 mg palmitoyl phosphatidyl choline (DPPC), 9 mg distearoyl phosphatidyl ethanolamine-PEG2000 (PEG-DSPE), and 8 mg cholesterol. The liposomes are dispersed in 10% sucrose buffered with phosphate buffer at a pH of 7.4.

The formulation is prepared by mixing the lipid constituents with an aqueous solution of the corticosteroid followed by repeated high-shear homogenization to reduce the size of the formed vesicles. Unencapsulated corticosteroid is removed by tangential flow filtration. Sterilization takes place by dead-end filtration using 0.2 micrometer filter membranes.

The formulation is subject to the following characterization and quality controls: particle size and polydispersity index (100 nm and <0.1 respectively as measured by dynamic light scattering), content of prednisolone and lipid excipients as measured by HPLC assays, sterility and pyrogenicity (the latter determined with the LAL assay (Biowhittaker, Walkersville, Md.)), and solvent residual testing. All raw material purchased is GMP-certified and the liposome manufacturing is performed under GMP conditions.

Patients

To evaluate the therapeutic activity of the prednisolone PEG-liposomal formulation in inflammatory disease, 16 consenting patients with active RA were enrolled in a clinical trial, in which 8 patients were treated once with 150 mg intravenously infused prednisolone-PEG-liposomes (approximately 2 mg/kg body weight of prednisolone) and 8 patients with an equipotent dose of 120 mg methylprednisolone depot formulation (intramuscular). Criteria for eligibility were as follows: age ≥18 years, RA according to the revised 1987 ARA criteria (Arnett F C, et al. 1988), active disease as defined by a Modified Disease Activity Score (DAS 28, Prevoo M L, et al. 1995)≥3.2 at the screening visit.

Exclusion criteria included abnormal renal, liver or hematological tests, current pregnancy, breastfeeding, infections or malignancies, clinically severe or unstable medical conditions and endocrine disorders. Oral GCs were not permitted within 2 weeks prior to study entry, intra-articular or intramuscular GCs were not allowed within 8 weeks prior to baseline and therapy with disease modifying anti-rheumatic drugs (DMARD) had to be stable within 12 weeks prior to trial initiation.

Study Protocol

After satisfying the in- and exclusion criteria, the administration of the study medication was planned. On day 1, patients were admitted to the ward where they received prednisolone PEG-liposomes/placebo or methylprednisolone/placebo. After baseline, patients were assessed weekly for up to 12 weeks. Each visit included clinical evaluation, assessment of the disease activity, vital signs, safety assessments, and blood sampling. The disease activity was measured by the same assessor using the Disease Activity Score (DAS28), and the response to therapy using the European League Against Rheumatism (EULAR) criteria (Zandbelt M M, et al. 2001; Van Gestel A M, et al. 1996). Disease flare was defined by an increase of the DAS28 of >1.2 or an increase of the DAS of 0.6-1.2 if this resulted in a DAS28 of >5.1, on the weekly assessments (Den Broeder A A, et al. 2002).

Data Analysis

The DAS 28 score was the primary outcome measure to test the efficacy of the trial intervention. Type I error was controlled at a significance level of 0.05 for the analysis of the primary outcome. Several secondary efficacy measures were analyzed to confirm the findings of the primary measure. These included the individual components of the DAS, the patient assessment for pain, the physician assessment for disease activity. As this was a trial with a limited number of patients, most analyses were descriptive only. Where statistical analysis could be applied the two sample t-test was used.

Results

Out of 16 patients, 14 patients (7 in each group) were evaluated for efficacy. A pronounced therapeutic improvement was found during the first weeks after treatment in the test medication (prednisolone PEG-liposomes) group during the first weeks after treatment. In the reference medication group (intramuscular methylprednisolone) a slower and more moderate therapeutic improvement is visible (FIG. 3).

The test medication group shows a higher percentage of responders according to the EULAR definition of therapeutic response. Interestingly, only patients in the test medication group experienced a good EULAR response (FIG. 4). In the reference medication the responses that were observed are only moderate. The intensity of pain was measured on a 100 mm line ranging from "no pain" to "extreme pain". The pain improved better and decreased more rapidly in the LCLP group (FIG. 5). A significantly better efficacy of the trial medication at the level of the "Investigator's evaluation of RA activity" was found as compared to the control medication.

The safety analysis showed comparable pattern of adverse events in both treatment groups. There was one serious adverse event (a mild infusion reaction) probably related to the trial medication. The trial medication did not raise further toxicity concerns.

Figure 6A:
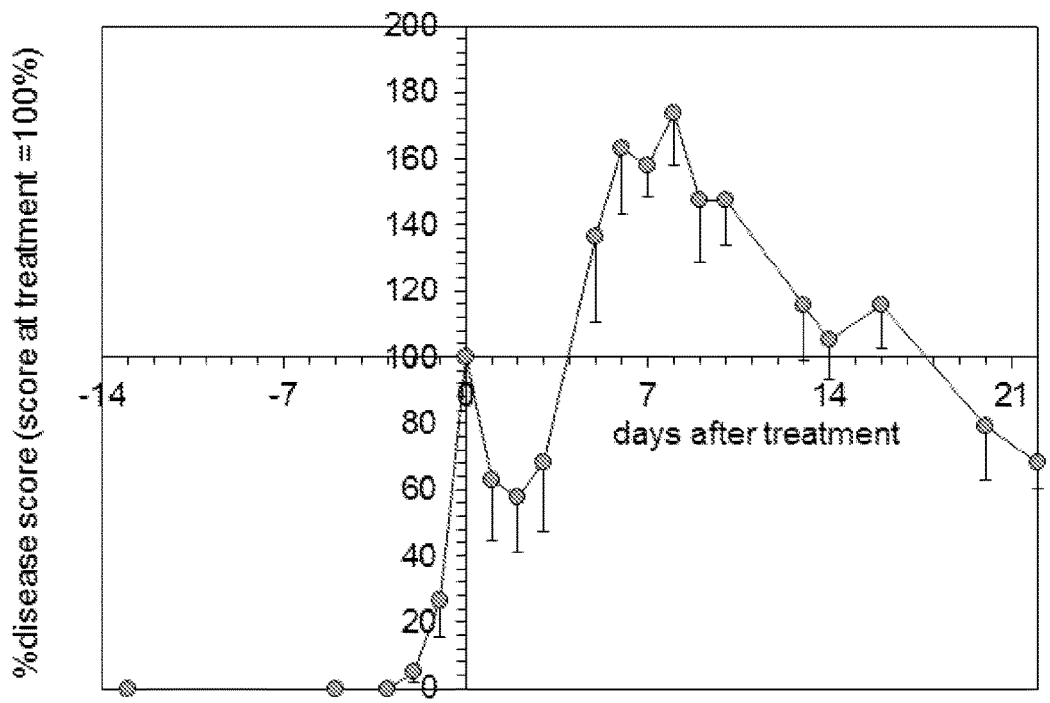
Figure 6B:
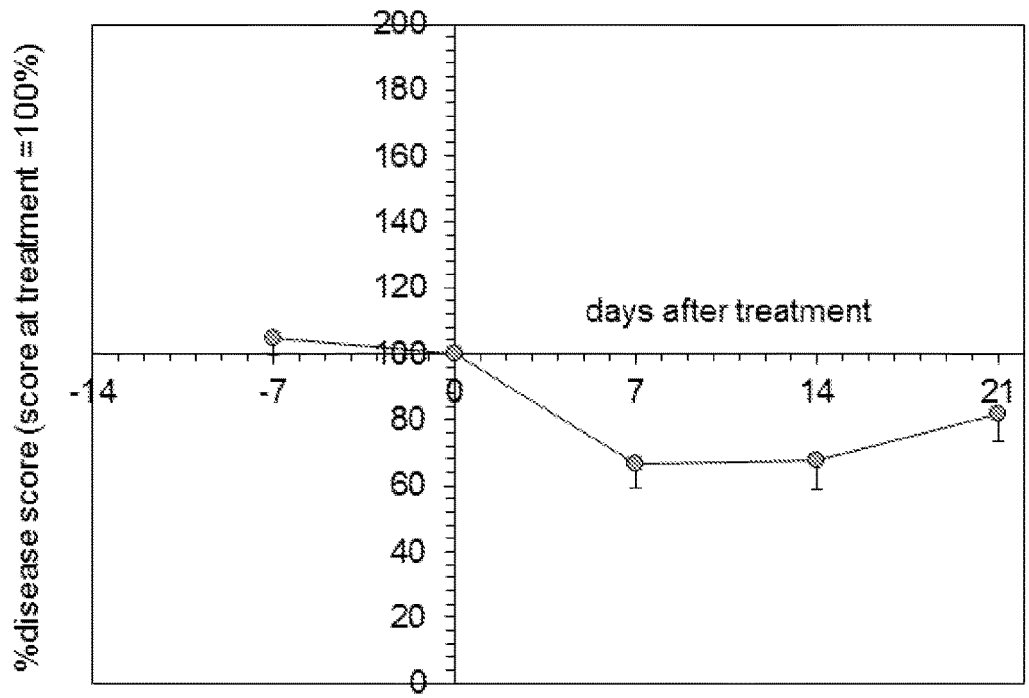

Interestingly the efficacy of 2 mg/kg prednisolone PEG-liposomes in the human study proved to be much more prolonged as compared to the efficacy of the same dose in rat experimental arthritis, which did not last longer than a few days. FIG. 6A shows the efficacy of a single treatment with 2 mg/kg liposomal prednisolone in rat arthritis and FIG. 6B shows the effect at the level of arthritic inflammation in humans (for the purpose of comparison the baseline value at the day of treatment was defined as 100%).

Figure 7A:
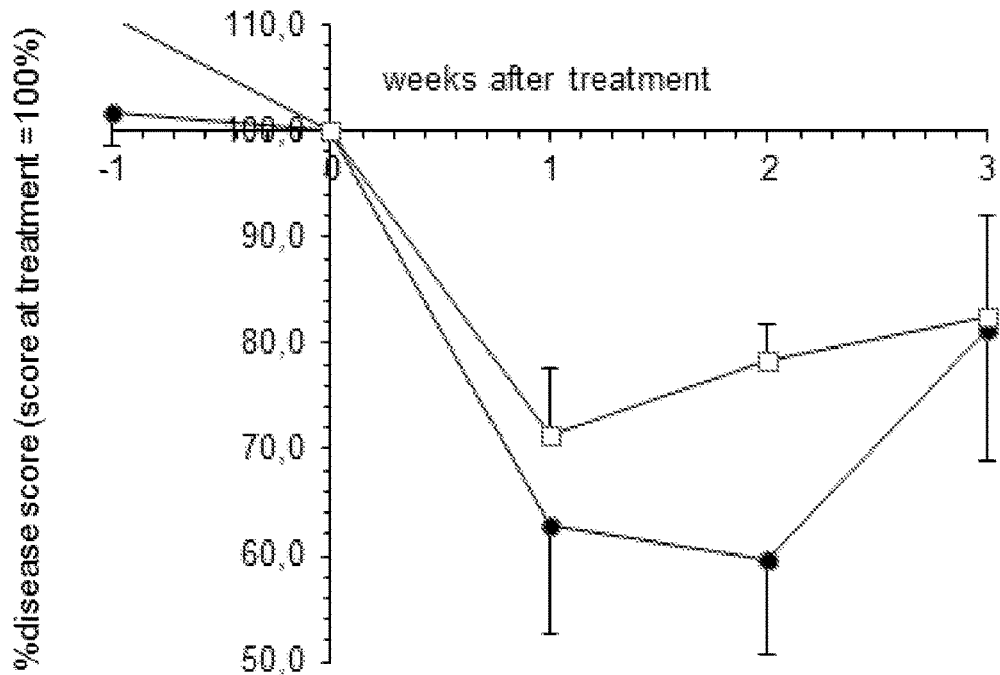
Figure 7B:
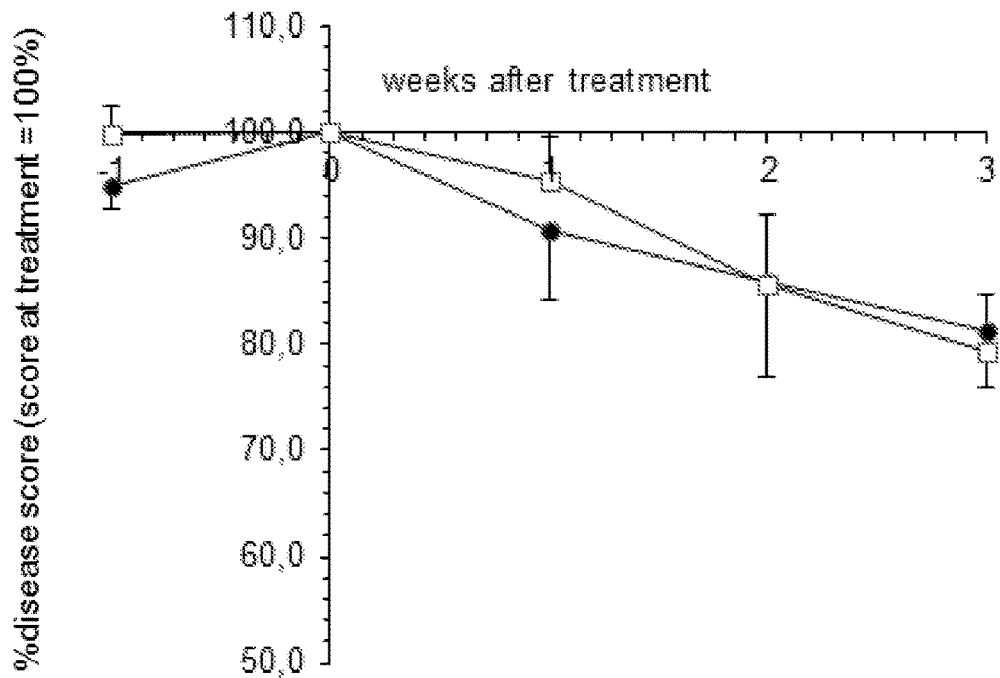

FIG. 7 shows the therapeutic effects of test medication and reference medication for patients receiving chronic therapy with methotrexate and patients not receiving such therapy. Patients who are under chronic therapy with methotrexate are more sensitive to the therapy with liposomal prednisolone than patients that do not take methotrexate or other disease modifying agents (FIG. 7A). However, patients who received reference medication (intramuscular methylprednisolone) did not show a better response in combination with methotrexate than patients with reference medication without methotrexate (FIG. 7B).

Example 3

Human Inflammatory Bowel Disorder Study

Formulation

Prednisolone containing PEG liposomes were prepared as described in Example 2.

Patients

Twenty subjects between the ages of 18 and 75 with active ulcerative colitis (UC) were selected during a 14-day screening phase according to the following main inclusion/exclusion criteria: ≥18 to 75 years of age, documented history of UC (at least 6 months) as assessed by endoscopy and confirmed by histological measurements, a Mayo score ≥5 with endoscopic sub-score of ≥2 and rectal bleeding sub-score ≥1 and stable medications (6-MP/azathioprine, 5-ASA, MTX, biologicals, and in good physical and mental health (other than the disease under study) as determined by medical history and physical examination.

Study Protocol

When a subject was randomized in the arm of investigational product, single infusions of 150 mg PEG-liposomal prednisolone sodium phosphate (Nanocort) IV in 250 mL saline over at least 1 hour were administered on Day 1 and at Day 15 (approximately 2 mg/kg body weight of prednisolone). When a subject was randomized in the placebo arm, single infusions of 250 mL saline (without Nanocort) over at least 1 hour were administered on Day 1 and at Day 15.

After baseline, patients were assessed weekly for up to 8 weeks. Each visit included clinical evaluation, assessment of the disease activity, vital signs, safety assessments, and blood sampling. The disease activity was measured as the % of subjects achieving clinical remission or response at Day 15, 29, 57 and 85 as measured by partial Mayo score in Nanocort versus placebo group, and by scoring the histopathological assessments on biopsies by microscopic evaluation (acute inflammation score and grading scale of inflammation) in Nanocort versus placebo group.

Results 7 patients have been enrolled so far. In the majority of the patients rapid and substantial beneficial therapeutic effects are seen.

REFERENCES

Arnett F C, Edworthy S M, Bloch D A, McShane D J, Fries J F, Cooper N S, Healey L A, Kaplan S R, Liang M H, Luthra H S, et al. The American Rheumatism Association 1987 revised criteria for the classification of rheumatoid arthritis. Arthritis Rheum 1988; 31: 315-324.

Den Broeder A A, Creemers M C, van Gestel A M, van Riel P L. Dose titration using the Disease Activity Score (DAS28) in rheumatoid arthritis patients treated with anti-TNF-alpha. Rheumatology (Oxford) 2002; 41:638-642.

Metselaar J M, Wauben M H, Wagenaar-Hilbers J P, Boerman O C, Storm G. Complete remission of experimental arthritis by joint targeting of glucocorticoids with long-circulating liposomes. Arthritis Rheum 2003; 48(7):2059-66.

Prevoo M L, van 't H of M A, Kuper H H, van Leeuwen M A, van de Putte L B, van Riel P L. Modified disease activity scores that include twenty-eight-joint counts. Development and validation in a prospective longitudinal study of patients with rheumatoid arthritis. Arthritis Rheum 1995; 38: 44-48.

Van Gestel A M, Prevoo M L, van 't H of M A, van Rijswijk M H, van de Putte L B, van Riel P L. Development and validation of the European League Against Rheumatism response criteria for rheumatoid arthritis. Comparison with the preliminary American College of Rheumatology and the World Health Organization/International League Against Rheumatism Criteria. Arthritis Rheum 1996; 39:34-40.

Zandbelt M M, Welsing P M, van Gestel A M, van Riel P L. Health Assessment Questionnaire modifications: is standardisation needed? Ann Rheum Dis 2001; 60: 841-845.

The invention claimed is:

1. A method for treating rheumatic disease or inflammatory bowel disorder, comprising intravenously administering to a human in need thereof liposomes comprising prednisolone, and having a mean particle diameter ranging from 40-200 nm,
    the liposomes having a composition comprising:
        (i) 0-50 mol % of cholesterol,
        (ii) 50-90 mol % of non-charged vesicle-forming lipids comprising saturated alkyl chains,
        (iii) 0-10 mol % of amphipathic vesicle-forming lipids coupled to polyethylene glycol, and
        (iv) 1-10 mol % of a negatively charged vesicle-forming lipid;
    wherein the prednisolone is administered at a dose of at most 5 mg/kg body weight, and;

wherein the liposomes are administered at most once per two weeks.

2. The method according to claim 1, further comprising administering a second, free corticosteroid at most once per two weeks.

3. The method according to claim 1, wherein the method further comprises administering an agent selected from the group consisting of methotrexate, hydroxychloroquine, leflunomide, cyclophosphamide, 5-fluorouracil, a 5-ASA agent, 6-mercaptopurine, mycophenolate mofetil, or azathioprine.

4. The method according to claim 3, wherein the human is administered a single treatment with the liposomes following a flare of the inflammatory disorder.

5. The method according to claim 3, wherein the agent is administered as part of maintenance therapy for the inflammatory disorder.

6. The method according to claim 1, wherein the liposomes comprise 2.5 to 10 mol % of negatively charged vesicle-forming lipids and/or 2.5 to 10 mol % of PEGylated lipids.

7. The method according to claim 1, further comprising administering an additional corticosteroid selected from the group consisting of dexamethasone and methylprednisolone.

8. The method according to claim 1, further comprising administering an additional corticosteroid selected from the group consisting of budesonide, flunisolide and fluticasone propionate.

9. The method according to claim 1, wherein the prednisolone is administered at a dose of at most 3 mg/kg body weight.

10. The method according to claim 1, wherein the prednisolone is administered at a dose of at most 2 mg/kg body weight.

11. The method according to claim 1, for treating inflammatory bowel disease.

12. The method according to claim 1, for treating rheumatic disease.

13. The method according to claim 1, wherein the rheumatic disease is rheumatoid arthritis.

* * * * *